United States Patent [19]

Waterstrat

[11] 4,078,921

[45] Mar. 14, 1978

[54] METHOD FOR ELIMINATING GAMMA$_2$ PHASE FROM DENTAL AMALGAM AND IMPROVED DENTAL AMALGAM COMPOSITION

[75] Inventor: Richard M. Waterstrat, Gaithersburg, Md.

[73] Assignee: American Dental Association Health Foundation, Washington, D.C.

[21] Appl. No.: 713,849

[22] Filed: Aug. 12, 1976

Related U.S. Application Data

[63] Continuation-in-part of Ser. No. 617,594, Sep. 19, 1975, Pat. No. 4,018,600.

[51] Int. Cl.$^2$ .......................... C22C 5/06; C22C 7/00
[52] U.S. Cl. .................................. 75/169; 75/173 R; 75/173 C
[58] Field of Search .................. 75/173 R, 173 C, 169

[56] References Cited

U.S. PATENT DOCUMENTS

| | | | |
|---|---|---|---|
| 1,970,319 | 8/1934 | Kern | 75/173 R |
| 3,954,457 | 5/1976 | Weikel | 75/173 C |
| 3,997,328 | 12/1976 | Greener | 75/173 C |
| 3,997,329 | 12/1976 | Aliotta et al. | 75/173 C |
| 4,018,600 | 4/1977 | Waterstrat | 75/173 R |

FOREIGN PATENT DOCUMENTS

| | | | |
|---|---|---|---|
| 949,063 | 8/1949 | France | 75/173 R |
| 8,552 | 3/1970 | Japan | 75/173 R |
| 112,902 | 1/1945 | Sweden | 75/173 R |

*Primary Examiner*—C. Lovell
*Attorney, Agent, or Firm*—Allegretti, Newitt, Witcoff & McAndrews

[57] ABSTRACT

An improved alloy for a dental amalgam includes silver and tin and the additional element, manganese. The alloy is comprised of a minimum of about 60% by weight silver, a maximum of about 20% by weight manganese and the balance tin. Various amounts of other constituents known to those in the art such as gold, copper, zinc and mercury may be included.

4 Claims, No Drawings

METHOD FOR ELIMINATING GAMMA$_2$ PHASE FROM DENTAL AMALGAM AND IMPROVED DENTAL AMALGAM COMPOSITION

The invention described herein was made in the course of work under a grant or award from the Department of Health, Education and Welfare.

This is a continuation-in-part of copending application Ser. No. 617,594, filed Sept. 19, 1975, now U.S. Pat. No. 4,018,600.

BACKGROUND OF THE INVENTION

This invention relates to an alloy for a dental amalgam and, more particularly, to a new class of such alloys which include silver, tin and manganese.

Amalgams are presently the principal material used by dentists for restoration of decayed teeth. About 75% of dental restorations are by amalgams. Amalgams are plastic at normal room and body temperature for a few minutes before they harden. Little or no change in volume occurs as a result of becoming hard. Amalgams combine the characteristics of high compressive and moderate tensile strength with the ability to withstand the corrosive environment defined by the mouth. Additionally, they are substantially non-toxic.

Generally, the alloy from which amalgams are made includes a mixture of silver and tin. The American Dental Association has established various standards for such alloys. Following is the American Dental Association specification for compositions of alloys used in making amalgams:

| Silver Min wt % | Tin Max wt % | Copper Max wt % | Zinc Max wt % | Mercury Max wt % |
|---|---|---|---|---|
| 65 | 29 | 6 | 2 | 3 |

The above composition standard was adopted by the American Dental Association effective June 1, 1970 and is also identified as American National Standard No. Z156.1-1970. Incorporated herewith by reference is the publication entitled "Guide to Dental Materials and Devices", Seventh Edition 1974–1975, copyright 1974, American Dental Association. Particular attention is directed to chapter 3 of this reference entitled "Amalgam and Mercury" as well as Specification No. 1 of the A.D.A. specifications for dental materials.

Amalgam alloys complying with present specifications and standards are generally silver-tin alloys containing approximately three parts of silver and one part of tin. This alloy is often referred to as the gamma phase ($\gamma$) or Ag$_3$Sn. In practice, the powdered alloy and mercury are subjected to trituration, thereby facilitating a reaction between mercury and the alloy. The mercury combines with the alloy to form new solid phases from the pulverized and triturated amalgam.

The chemical reaction during amalgamation may be described as follows:

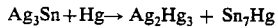

Thus, in addition to a gamma$_1$ phase ($\gamma_1$) (Ag$_2$Hg$_3$), a tin-mercury phase, often referred to as the gamma$_2$ phase ($\gamma_2$), is formed. The gamma$_2$ phase has a simple hexagonal crystal structure and may contain 5 to 12% atomic percent mercury. The composition for this phase is uncertain; though, the phase is often designated as Sn$_7$Hg or Sn$_8$Hg.

The tin-mercury phase in a dental amalgam is known as a weak constituent relative to the silver-tin and silver-mercury phases. Nonetheless, the gamma$_2$ phase may comprise up to 10% of the amalgam. The gamma$_2$ phase has been associated with poor corrosion resistance and excessive flow or creep under an applid stress. To overcome the deficiencies noted in the gamma$_2$ phase, the subject matter of the present invention has been developed.

SUMMARY OF THE INVENTION

Briefly, the invention comprises an improved alloy for amalgams wherein manganese is used in silver-tin based dental alloys to react with the tin during amalgamation and thus reduce or eliminate the tendency of these alloys to form the undesirable gamma$_2$ phase.

Thus, it is an object of the present invention to provide an improved alloy for dental amalgams.

It is a further object of the present invention to provide an improved alloy for dental amalgams utilizing manganese in order to improve corrosion resistance and reduce excessive flow or creep.

Still another object of the present invention is to provide an improved alloy for dental amalgams which is inexpensive and effective with an ability to perform acceptably and meet standard specifications.

These and other objects, advantages and features will be set forth in the detailed description which follows.

DESCRIPTION OF THE PREFERRED EMBODIMENT

The alloy of the present invention utilizes manganese in combination with a silver-tin dental alloy. The manganese reacts with the tin during the amalgamation process, thus reducing or eliminating the tendency of such alloys to form the undesirable gamma$_2$ phase during amalgamation.

As an example of the particular class of compounds which result during the amalgamation of the alloy, the following formulation is set forth:

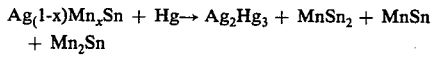

The relative amounts of Ag$_2$Hg$_3$ and MnSn$_2$ (MnSn, Mn$_2$Sn) which are formed depend upon the amount of manganese. If no manganese is present, then the reaction which occurs is the standard amalgam reaction recited above in the Background of the Invention. Increased amounts of manganese will decease progressively the amount of tin which is available to form the gamma$_2$ phase.

Typically, in such alloys, an amount of the original alloy particles (Ag$_3$Sn) remains unreacted. Thus, one normally obtains a solid mixture of the products of the reaction together with residual, unreacted alloy particles. A certain amount of manganese remains in the unreacted portion and thus unavailable for reaction with tin. It is therefore difficult to predict exactly how much manganese is needed to prevent the formation of the gamma$_2$ phase. A lower limit of the amount, however, can be calculated by assuming that all of the manganese is available for reaction. On this basis, it is estimated that about 8% manganese should suffice to eliminate the gamma$_2$ phase.

Additions of manganese in excess of the amount required to eliminate the gamma$_2$ phase may provide beneficial effects. Alloys have been tested containing 12% manganese. Such alloys possessed excellent resistance to creep or flow as compared with an 8% manganese alloy of the present invention or with other commercial amalgam alloys. Preliminary tests also indicate that amalgams prepared from the above-described alloys are equally as corrosion resistant as other commercial alloys. Following are examples of alloys and specific tests performed:

EXAMPLE No. 1

Homogeneous mixture comprising 62% silver, 12% manganese and 26% tin was prepared by atomization of the molten metal alloy. This resulted in the formation of approximately spherical particles having a particle size between 325 and 400 mesh. An amalgam was prepared from the alloy using a 6.2:6 ratio of mercury to alloy. The amalgam was prepared in a commercial amalgamator in accordance with conventional procedures. All tests were conducted using methods described in the American Dental Association specification No. 1 referenced above. Corrosion resistance was determined to be as good as many of the prior art amalgams. Resistance to creep or flow was improved relative to prior art amalgams. Typical comparative data is set forth below with the amalgam of the 12% alloy of the present invention listed first:

| Alloy | ADA Flow Test[1] | Dimensional Change | 24 hr. Diam.[3] Tensile Strength |
|---|---|---|---|
| 12% Mn alloy | 0.16 to 0.03% | 0 to +4 | 5700 to 7500 psi |
| Dispersalloy[4] | 0.6% | +13 | 7300 psi |
| 10% Au alloy | | +20 | 7750 to 8900 psi |
| Optalloy[5] | 1.09% | −7 | 10,700 to 11,100 psi |
| Velvalloy[6] | 0.81% | −12 | |
| Spheralloy[7] | 0.86% | −17 | |

| Alloy | 15 min. Diam.[2] Tensile Strength |
|---|---|
| 12% Mn alloy | 1760–1970 psi |
| Dispersalloy | 300 psi |
| Optalloy | 800 psi |
| Velvalloy | 550 psi |
| Spheralloy | 650 psi |

This amalgam was sectioned, polished and submitted to examination by X-ray area scanning in an electron microprobe. The characteristic X-ray emission from tin, manganese and silver was mapped separately on the same area of the sample at a magnification of about 1000X. This technique revealed that each residual spherical particle of the gamma$_1$ phase was surrounded by a layer of manganese-tin compound. There was no evidence of any tin-mercury compound. X-ray diffraction patterns of this amalgam were difficult to interpret dut to line overlaps but the strong-intensity line of the gamma$_2$ phase, usually present in patterns from conventional amalgams, was in this case replaced by a weak-intensity line.

1. American Dental Association Specification No. 1 flow test.
2. American Dental Association Specification No. 1 tensile strength.
3. The same test as defined by No. 2, except after 24 hours.
4. Trade name for amalgam alloy sold by America Silver & Mercury Producers.
5. Trade name for amalgam alloy sold by L. D. Caulk Co., Division of Dentsply International, Inc.
6. Trade name for amalgam alloy sold by S. S. White Division, Pennwalt Corp.
7. Trade name for amalgam alloy sold by Kerr Mfg. Co.

EXAMPLE No. 2

The same experiment was performed using an alloy including 66% silver, 8% manganese and 26% tin. Substantially identical results were observed.

Additional experiments have shown that the amount of manganese may be increased to 20% by weight without adversely affecting the efficacy of the invention. Moreover, it is also possible to mix the improved manganese alloy with previously existing amalgam alloys to achieve the improvement of the invention. For example, a prior art alloy including a minimum of 65% by weight silver, a maximum of 29% by weight tin, a maximum of 6% by weight copper, a maximum of 2% by weight zinc and a maximum of 3% by weight mercury may be combined with the alloy of the present invention.

This mixture of alloys may then be formed as an amalgam by proper trituration of mercury and the two alloys. The permitted ratio of the two alloys extends over the full range of possible mixtures. A preferred ratio provides an effective amount of manganese equal to about 10 to 12% of the total weight of the mixed alloys.

The improved manganese alloy of the present invention may also be mixed with more than one additional dental alloy. Thus, two or more dental amalgam alloys may be mixed with the improved alloy of the present invention to provide a composite alloy formable as an amalgam by proper trituration.

Additionally, the manganese component of the alloy of the present invention may be replaced, in part, by copper or gold. For example, about one to thirty parts by weight copper may be substituted for part of the manganese and/or silver.

The alloy may also be preamalgamated. That is, the alloy may contain a small percentage (1-5% by weight) of mercury. This mercury is included as part of the alloy before amalgamation. The preamalgamated alloy may then be formed as an amalgam by proper trituration of additional mercury and the alloy.

In summary, the contemplated range of alloy constituents is set forth below.

| Range (by weight) | Preferred (by weight) |
| --- | --- |
| Tin (Sn) - 16–29% | 26 ± 0.1% |
| Silver (Ag) - 60–83% | about 65 ± 3% |
| Manganese (Mn) - 2%–20% | about 10 ± 3% |
| Copper (Cu) - 1–30% as a substitute for part of the manganese and/or silver | |
| Mercury (Hg) - 1–5% as a preamalgam | |
| Gold (Au) - 1–10% as a substitute for part of the manganese and/or silver | |

It is clear that changes to the composition may be effected and stil remain within the scope of the invention. Thus, the amalgamation procedure may call for additional mercury. Other alloying agents such as copper, zinc or mercury may be included in the alloy. The invention, therefore, is to be limited only by the following claims and their equivalents.

What is claimed is:

1. An improved alloy for a dental amalgam consisting essentially of at least 2% up to 20% by weight manganese and the balance 60–83% by weight silver and 16–29% by weight tin.

2. An alloy as set forth in claim 1 including 1–5% mercury as a preamalgam.

3. An alloy as set forth in claim 1 including one or more from the group of gold and copper in place of part of the manganese.

4. An alloy as set forth in claim 1 in combination with mercury to form an amalgam.

* * * * *

UNITED STATES PATENT OFFICE
CERTIFICATE OF CORRECTION

Patent No. 4,078,921  Dated March 14, 1978

Inventor(s) Richard M. Waterstrat

It is certified that error appears in the above-identified patent and that said Letters Patent are hereby corrected as shown below:

The term of this patent subsequent to April 19, 1994 has been disclaimed.

Signed and Sealed this

Fourth Day of July 1978

[SEAL]

Attest:

RUTH C. MASON
Attesting Officer

DONALD W. BANNER
Commissioner of Patents and Trademarks